(12) United States Patent
Fahrig et al.

(10) Patent No.: US 9,155,913 B2
(45) Date of Patent: Oct. 13, 2015

(54) ROBOTIC LINAC ADAPTATION (RLA) FOR THE IN-LINE MRI-LINAC CONFIGURATION

(75) Inventors: Rebecca Fahrig, Palo Alto, CA (US); Dragos E. Constantin, Los Altos, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/565,343

(22) Filed: Aug. 2, 2012

(65) Prior Publication Data
US 2013/0035584 A1    Feb. 7, 2013

Related U.S. Application Data

(60) Provisional application No. 61/574,432, filed on Aug. 2, 2011, provisional application No. 61/626,009, filed on Sep. 19, 2011.

(51) Int. Cl.
*A61B 5/055*   (2006.01)
*A61N 5/10*    (2006.01)

(52) U.S. Cl.
CPC .............. *A61N 5/1083* (2013.01); *A61B 5/055* (2013.01); *A61N 5/1067* (2013.01); *A61N 2005/1055* (2013.01)

(58) Field of Classification Search
CPC .... H01J 3/027; H01J 3/029; H05H 2007/084; H05H 7/08; A61B 5/055; A61N 2005/1055; A61N 5/1067; A61N 5/1083
See application file for complete search history.

(56) References Cited

U.S. PATENT DOCUMENTS

2011/0218420 A1*  9/2011  Carlone et al. ................ 600/411

* cited by examiner

*Primary Examiner* — Ruth S Smith
(74) *Attorney, Agent, or Firm* — Lumen Patent Firm

(57) ABSTRACT

An in-line MRI-linac apparatus is provided that includes an MRI magnet of an MRI scanner, where the MRI magnet generates a magnetic field, where the magnetic field has a quasi-uniform fringe field, where the fringe field is proximal to an axis of symmetry of the MRI magnet, and a magnetically unshielded dynamically moveable linac that includes a treatment beam that is aligned with field lines of the fringe field in a quasi axial symmetric configuration, where a position of the linac in the fringe field continuously adapts according to a target position to enable continuous dose delivery to the target.

1 Claim, 8 Drawing Sheets

ROBOTIC LINAC ADAPTATION (RLA) FOR THE IN-LINE MRI-LINAC CONFIGURATION

CROSS-REFERENCE TO RELATED APPLICATIONS

This application claims priority from U.S. Provisional Patent Application 61/574,432 filed Aug. 2, 2011, which is incorporated herein by reference. This application claims priority from U.S. Provisional Patent Application 61/626,009 filed Sep. 19, 2011, which is incorporated herein by reference.

STATEMENT OF GOVERNMENT SPONSORED SUPPORT

This invention was made with Government support under contract T32-CA09695 awarded by National Institutes of Health. The Government has certain rights in this invention.

FIELD OF THE INVENTION

The current invention relates generally to radiotherapy. More particularly, the invention relates to an in-line MRI-linac apparatus having an unshielded dynamically moveable linac that continuously adapts according to a target position to enable continuous dose delivery to the target.

BACKGROUND OF THE INVENTION

The ideal image guidance strategy in radiation therapy is to have real-time volumetric and position information of the tumor and surrounding healthy tissue during the treatment itself. One approach is to use magnetic resonance imaging (MRI), which is a non-invasive technique that not only allows real time volumetric imaging, but also provides exquisite soft tissue contrast to differentiate cancerous from healthy tissue. To date two base MRI-linac configurations were proposed, i.e. the in-line and the perpendicular configurations, which are defined by the relative orientation of the medical linac with respect to the main magnetic field of the MRI scanner. Regardless the configuration the relative position between the linac and the MRI isocenter is fixed with the linac pointing at it. This fact limits the use of the medical linac to gating or dynamic multileaf collimator (DMLC) or a combination of these two radiation treatment modalities. What is needed is an apparatus that continuously adapts according to a target position to enable continuous dose delivery to the target.

SUMMARY OF THE INVENTION

To address the needs in the art, an in-line MRI-linac apparatus is provided that includes an MRI magnet of an MRI scanner, where the MRI magnetic includes a magnetic field, where the magnetic field has a quasi-uniform fringe field, where the fringe field is proximal to an axis of symmetry of the MRI magnet, and a magnetically unshielded dynamically moveable linac that includes a treatment beam that is aligned with field lines of the fringe field in a quasi axial symmetric configuration, where a position of the linac in the fringe field continuously adapts according to a target position to enable continuous dose delivery to the target.

In one aspect of the invention, the linac includes an electron gun, where a geometry of a cathode, an anode and a focusing electrode of the electron gun is determined according to the MRI magnetic field.

According to another aspect of the invention, the linac includes an electron gun that is magnetically unshielded.

In a further aspect of the invention, the moveable linac is configured such that movement of the linac does not perturb a homogeneity of the fringe field lines of the MRI magnet.

In yet another aspect of the invention, the quasi axial symmetric configuration comprises a displacement between a symmetry axis of the MRI-linac apparatus and the treatment beam.

According to a further aspect of the invention, the target is located proximal to an isocenter the of in-line MRI-linac apparatus.

In another aspect of the invention, the treatment beam is injected to a straight-through linac waveguide.

According to a further aspect of the invention, the quasi axial symmetric configuration includes field line curvatures of the magnetic field that are greater than a length of a waveguide in the linac.

In yet another aspect of the invention the MRI magnet is unshielded, whereby the quasi-uniform fringe field is formed.

According to another aspect of the invention, the MRI scanner and the linac are electromagnetically coupled.

DETAILED DESCRIPTION

According to one embodiment, the invention includes an MRI-linac configuration, which can continuously adapt the linac orientation based on tumor position. This new configuration, called robotic linac adaptation (RLA), is based on in-line MRI-linac configuration, which does not use magnetic shielding for the electron gun and does not use magnetic shielding for the linac. In another embodiment a new electron gun geometry is provided that is capable to robustly function in the presence of high strength external magnetic field.

In one example, a specially designed electron gun together with a waveguide model for the Varian 600C linear accelerator (linac) are simulated in the fringe field of a 0:5 T open bore MRI magnet (GE Signa SP) which has a 60 cm gap between its poles. In this example, the linac is positioned along the magnetic field lines and it is displaced off the axis of symmetry of the magnet to account for the tumor displacement with respect to the isocenter of the system. The electron beam statistical characteristics at target button position are quantified as functions of linac displacement parameters.

For the specific elements considered in this example it was determined that the gun will experience fields of 0:187 T if the tumor is located in the system isocenter. However, it is shown that the gun can function in field strengths ranging from 0:172 T to 0:204 T which accounts for gun displacements of ±5 cm along the axis of symmetry from the central position. It is shown that for an axial symmetric arrangement of a straight through linac, i.e. no bending magnet, in an external magnetic field there is no need for magnetic shielding. It is shown that transverse tumor displacements as big as 10 cm from the MRI isocenter can be tracked by the linac.

The electron gun can operate in the presence of an aligned MRI magnet fringe field. It is shown using computer simulations that the electron gun can produce high quality beams, which can be efficiently injected into a straight through medical linac waveguide for an RLA MRI-linac configuration. The use of an MRI-linac machine in continuous regime such that the linac can follow the tumor motion is thus enabled.

According to one embodiment of the invention, a MRI-linac configuration capable of making full use of the positional information provided by the MRI scanner and adapt the linac orientation so it can track the tumor motion and continuously deliver dose is provided. This new MRI-linac configuration, called robotic linac adaptation (RLA) configuration, is an in-line MRI-linac configuration with no magnetic shielding. Besides traditional radiotherapy the RLA configuration can be used in any medical application that require precise image guidance for radiation delivery purposes, like stereotactic radiosurgery or radiosurgical cardiac ablation.

Figure 1:
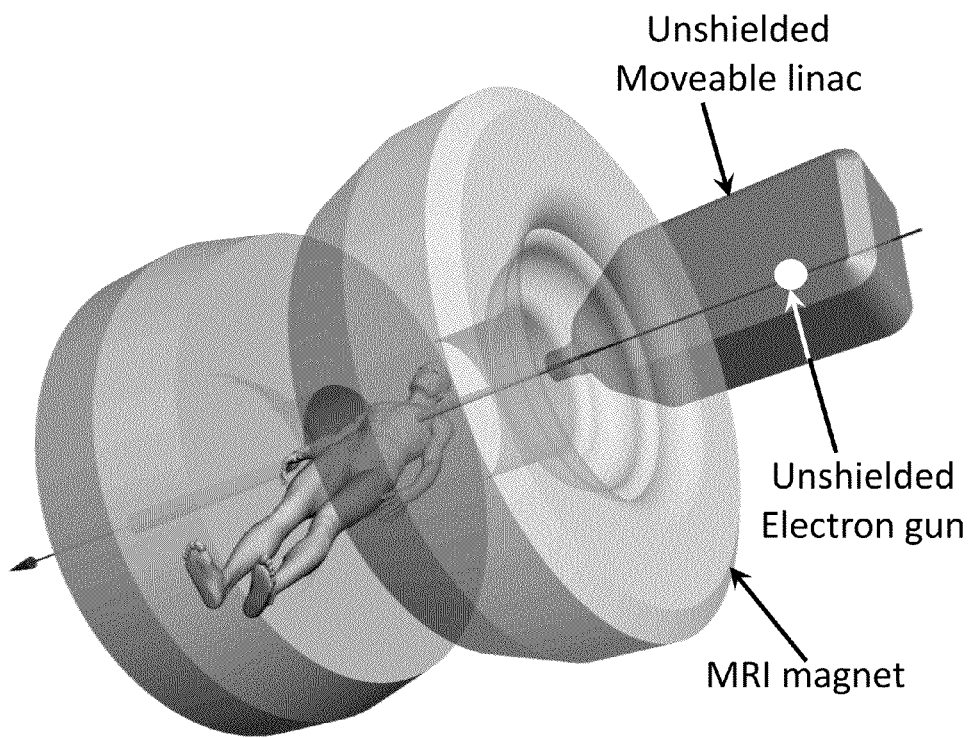
FIG. 1 shows a schematic representation of one embodiment of the in-line MRI and unshielded linac apparatus.

The RLA invention is based on the observation that an electron beam will stay confined in the presence of an axially symmetric field. The generalization includes relaxing the perfect axial symmetry condition and requires only that the linac is aligned with the field lines. According to one embodiment, this condition can be seen as a quasi-axial symmetry condition if the field line curvature is much bigger than the length on the linac waveguide. The absence of the magnetic shield allows the linac to move without perturbing the magnet homogeneity. In the example, it is assumed that all the magnetic components present in the linac construction were replaced with magnetically compatible parts. The mrT magnet is not shielded which makes the fringe field to be quasi uniform close to the magnet axis of symmetry despite its relatively high strength. Even if the fringe field has a high value in the range of interest, the relatively good homogeneity keeps the induced eddy currents in the linac and copper structures very small. Despite their tremendous medical benefits and potential to treat hard to treat cancerous sites, MRI-linacs are difficult to build as both the medical linac and the MRI scanner use electromagnetic fields to function, and arbitrarily placing these systems in close proximity may cause interactions which could degrade their functionality. The electromagnetic coupling between the systems reduces the degrees of freedom regarding possible orientations of the linac and MRI subsystems. One solution is to keep the relative position between the patient and each subsystem unchanged in the hybrid system; the main magnetic field is perpendicular to the treatment beam and thus to the electron beam. This configuration, referred to from now on as the perpendicular configuration, has no symmetry. Another solution with axial symmetry places an unsheilded linac and the MRI machines such that the electron beam path and the main field of the MRI system are in-line. This solution requires the relative position of the patient with respect to the MRI scanner to be changed, as shown in FIG. 1. Because the in-line design has axial symmetry one can employ Bush's theorem and conclude that in this case the external magnetic field will have no major impact on electron beam optics inside the accelerating waveguide in terms of defocusing effects. In fact the existence of the external axial field will cause magnetic confinement of the beam and this effect can be used to keep the electron beam focused along the accelerator waveguide. These properties of charged particles beams can be verified and quantified by computer simulations.

FIG. 1. Shows a schematic representation of one embodiment of the in-line unshielded MRI-linac apparatus. The treatment beam is in-line with the main magnetic field of the MRI magnet. The patient is positioned between the poles of the open bore MRI magnet in a perpendicular position with respect to the main magnetic field and the treatment beam. The whole MRI-linac apparatus rotates around the patient superior-inferior axis such that the main magnetic field of the MRI scanner and the treatment beam remain in-line, although the patient could alternatively be rotated in a sitting or lying position.

In contrast, for the perpendicular configuration one has to make sure the electron gun and the accelerating waveguide are magnetically shielded from the MRI magnet otherwise the Lorentz force will bend the electron beam and no acceleration will occur. The perpendicular design requires decoupling of the physics of the MRI scanner and the linac. Because the penumbra of a photon beam is reduced under the influence of external in-line magnetic fields provides an advantage of the current in-line invention over the perpendicular approach. For the in-line design, the phenomenon known as the electron return effect is reduced or eliminated thus allowing for a possible reduction in dose to the surrounding tissues. The schematic representations in FIG. 1 are close renderings of the real MRI scanner. The special geometry of this MRI magnet allowed the successful implementation of a hybrid MRI-fluoroscopy apparatus. Though not designed or optimized for this purpose, the mrT scanner nevertheless provides a reference lower bound of performance possible for a dedicated in-line MRI-linac. In this example, the magnetic field produced by this particular magnet is considered. The unshielded electron gun is not the only subsystem of an unshielded moveable medical linac whose behavior needs to be characterized in external magnetic fields. Other critical elements that have to be studied are the accelerating structure and the treatment head together with patient geometry. The modeling strategy uses the phase space information of the electron beam generated by the unshielded electron gun as the input for the simulation of the beam transport along the accelerating tube. Similarly, the end result of beam transport along the accelerating structure, i.e., the beam phase space information right before the tungsten target, constitutes the input for modeling the beam transport through the medical linac treatment head and patient geometry. The weakness of this approach is that the accuracy of each component will depend on the accuracy of the output from the previous step(s). However, the model provides a basis for an end to end simulation of a medical electron linac which also includes the treatment head and patient geometry.

Regarding the electron gun, since there is no magnetic shielding present for the linac, the electron gun geometry needs to be redesigned to allow its operation in external fields.

Figure 2:
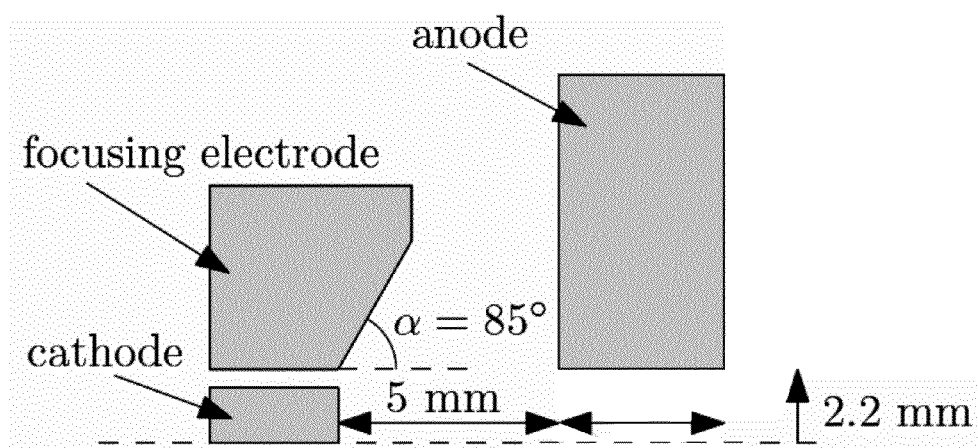
FIG. 2 shows an electron gun geometry, according to one embodiment of the invention.

It is necessary to model the modified electron gun together with the corresponding accelerating waveguide to ensure proper electron beam capture and acceleration when magnetic fields are present. In this example the Varian 600C linac for which there are published linac and electron gun models is considered. The redesign procedure involves two steps. First, modifications of the 0 T electron gun geometry are considered and the behavior of the altered electron gun geometry in external fields is characterized. Second, based on the observations gathered from the first step, a new electron gun geometry is generated and optimized to work at 0:19 T based on the results of the previous analysis. The value of the magnetic field of 0:19 T corresponds to the value of the magnetic field of the mrT magnet 1:3 m away from the isocenter. Because, the distance between the electron gun cathode, i.e. the electron emitting surface, and the linac tungsten target is roughly 0:3 m, this means that a 1:3 m distance between cathode and the MRI-linac isocenter places the linac target button at the standard distance of 1:0 m away from the isocenter. Electron beam generation and initial acceleration through the electron gun geometry was simulated with a full three dimensional (3D) model using SCALA (Vector Fields Ltd. OPERA-3d). The SCALA model includes the effect of the space charge interactions, which affect beams of charged particles and arbitrary three dimensional external magnetic fields can be taken into account. SCALA could also include the self magnetic fields generated by the beam. However, the simulations showed no change due to these fields especially in the presence of strong external magnetic fields and this effect can be neglected and it was not included in the simulation. In addition the simulation includes neither secondary electrons nor backscattered electrons as the main goal of the gun geometry design is to avoid these phenomena. Langmuir-Fry law was used to model the thermionic emission at cathode surface for the new electron gun geometry. This thermionic model is realistic enough to match experimental data and in the same time it is not too computationally intensive. This achieved a great balance between the simulation realism and the computation time. However, Child's law was used for the first step of the analysis to remain consistent with the original simulations performed with EGN2w (Stanford Linear Accelerator, CA). The electron beam transport in SCALA is simulated using macroparticles, which are defined as assemblages of many physical particles of the same type, e.g., electrons, which are treated as single units. The electron beam phase space was obtained by recording the individual contributions of any macroparticle, which crosses a plane perpendicular to the gun axis located at the gun exit position. The phase space information allowed the computation of the electron beam twiss parameters, which characterize the statistical properties of the electron beam. FIG. 2 shows one embodiment of a new electron gun geometry.

At 0 T the electron gun geometry was originally designed with EGN2w. The same electron gun was modeled with SCALA and a smaller cathode was considered based on the observation that the emitted current for the SCALA model was 20% higher than what was computed with EGN2w if the same geometry was used. The simulations show an increase in beam current of only 1:9% compared to the EGN2w. Also, the model with a smaller cathode gives a current, which is 16:6% smaller than the one computed with EGN2w. It is expected to see differences between the 2D axially symmetric EGN2w model and a full 3D SCALA model, however a 20% difference is symptomatic. Both, EGN2w and SCALA simulate the same physics and the models used are identical hence a small difference of roughly 2% is more normal.

Some of the beam characteristics, i.e. rms beam emittance and the Courrant-Snyder parameter α, dependence on the axial position were used to determine the beam injection point, i.e. the gun exit position.

According to a further embodiment of the invention, the guidance method is based on displacing the linac from the MRI axis such that locally the axial symmetry is quasi fulfilled and the treatment beam is aiming at the new position of the tumor. For this to work the field lines of the magnet have to be quasi uniform as presented in FIG. 3. Also, a short linac would help improve the degree of local symmetry.

Figure 3:
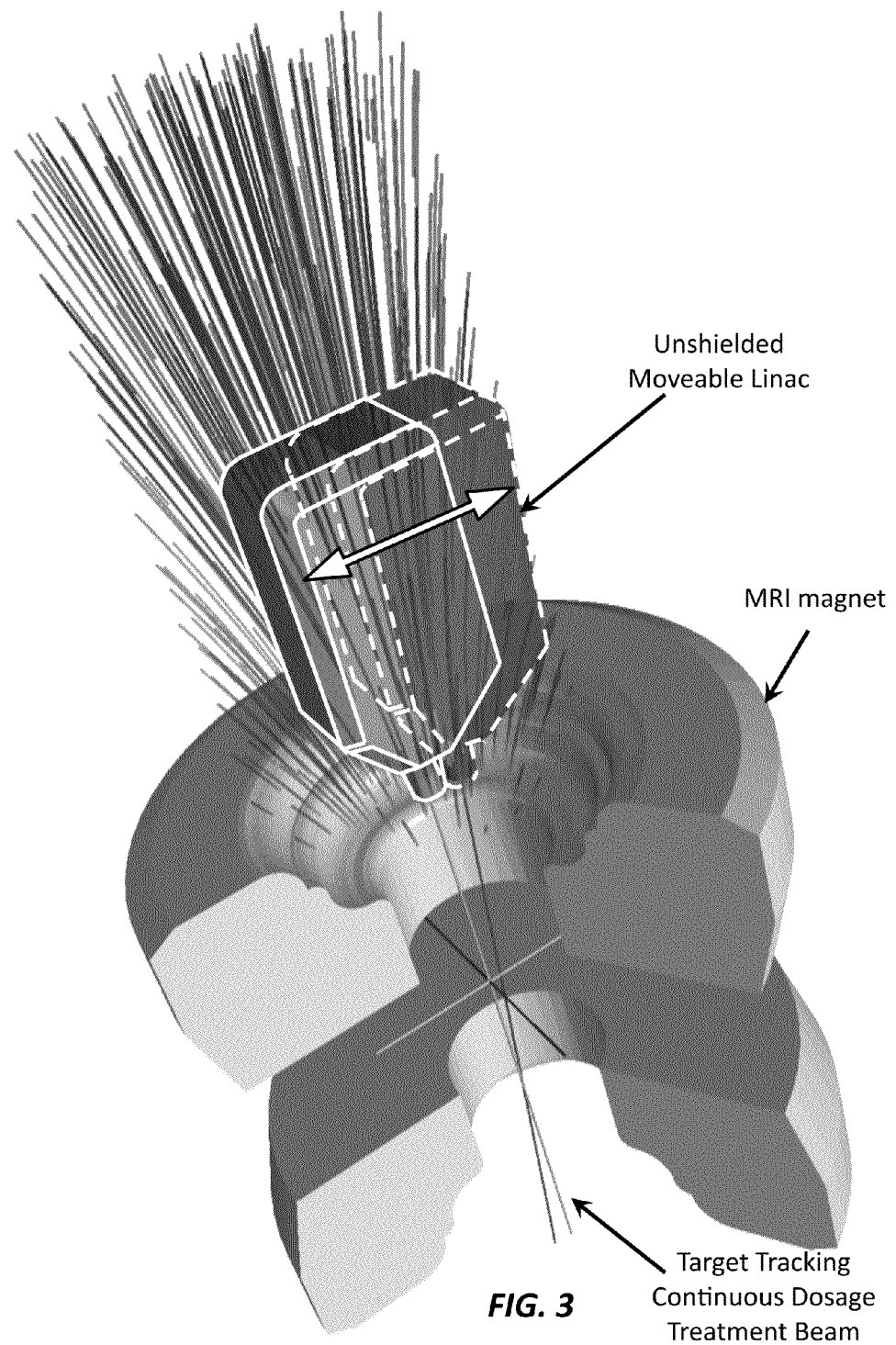
FIG. 3 shows a cutaway view of the open bore MRI scanner GE Signa SP or mrT, its fringe field lines and a CyberKnife-like treatment unit positioned off and on axis along the field lines of the magnet, according to one embodiment of the invention.

FIG. 3 shows a cutaway view of the open bore MRI scanner GE Signa SP or mrT, its fringe field lines and a CyberKnife-like treatment unit positioned off and on axis along the field lines of the magnet, according to one embodiment of the current invention. For the off axis configuration there is a small displacement between the isocenter of the MRI-linac apparatus and the treatment beam. For the purpose of the example, a Varian 600C linac model was used. The particle dynamics along the accelerating waveguide was simulated with PARMELA.

Figure 4:
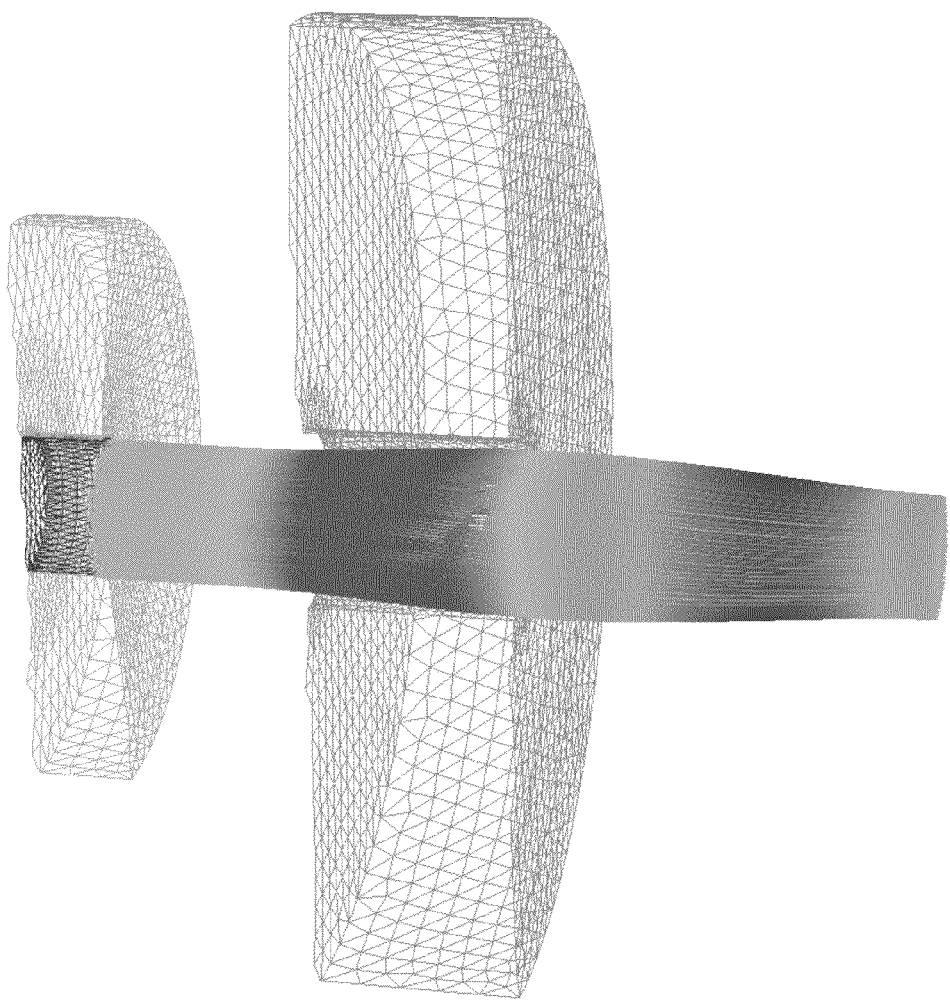
FIG. 4 shows the newly designed electron gun and its corresponding space charge solution, according to one embodiment of the invention.
Figure 5:
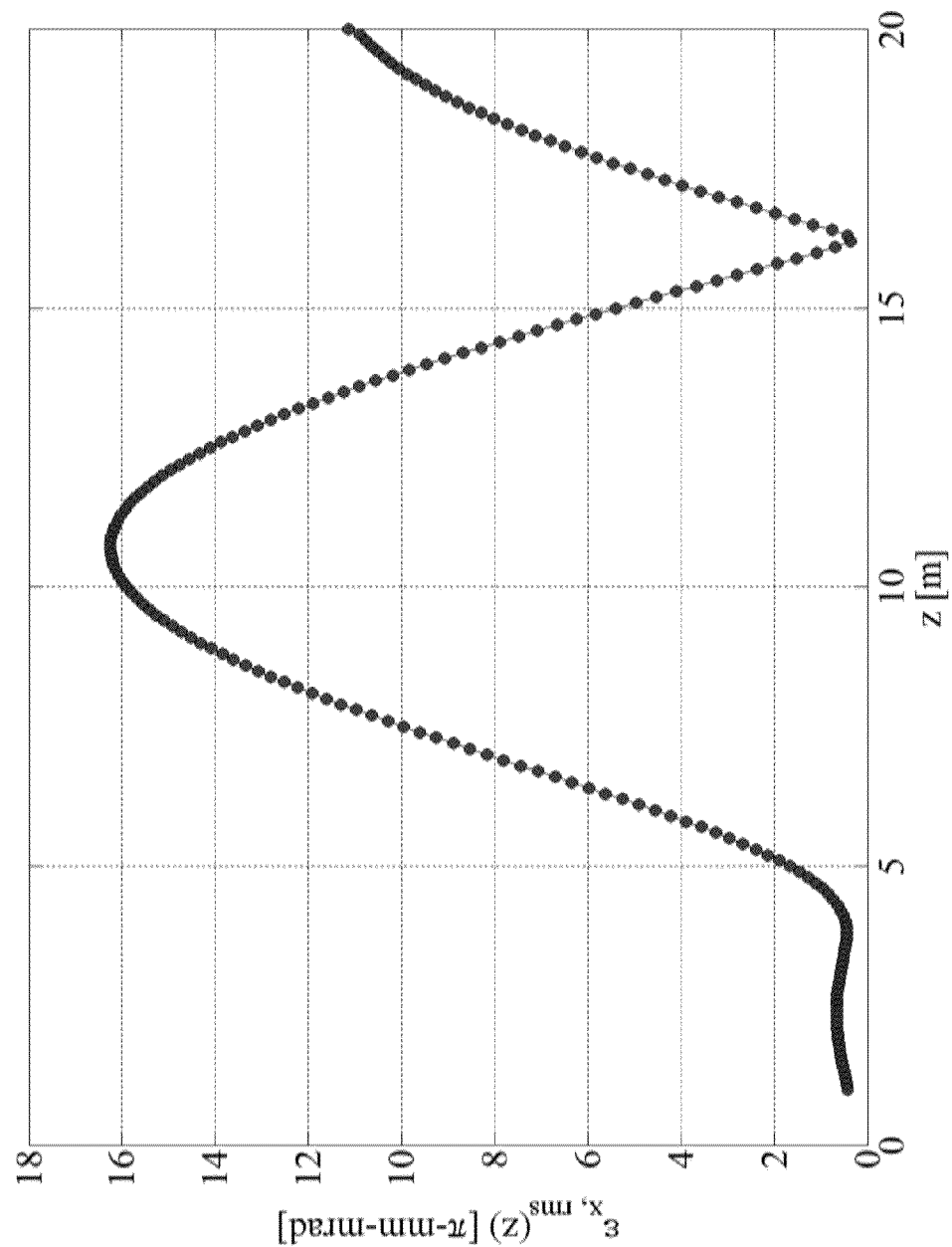
FIG. 5 shows a graph of the transverse rms emittance as a function of axial coordinate, i.e. along gun axis, where a minimum is reached 4.4 mm away from the cathode, according to one embodiment of the invention.
Figure 6:
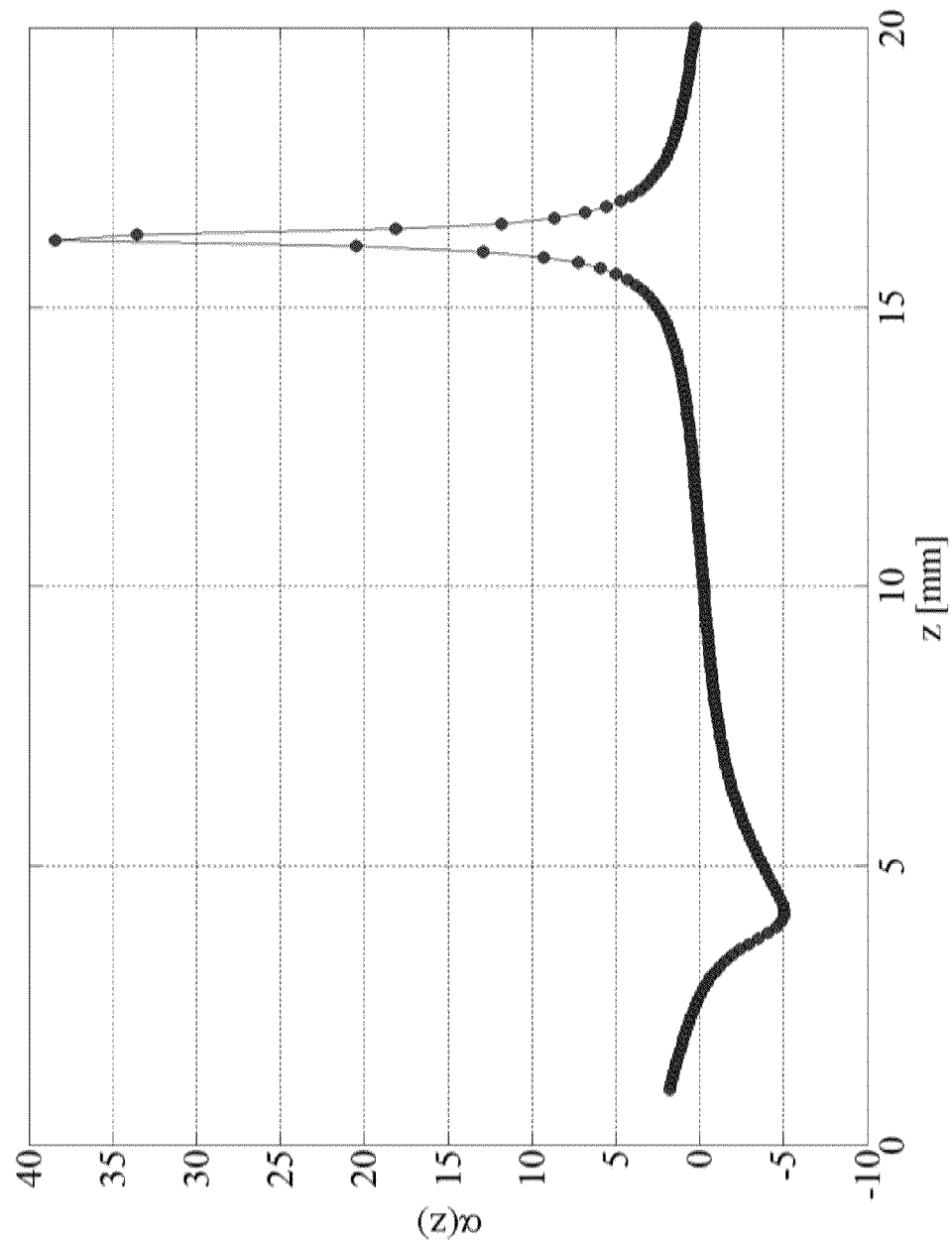
FIG. 6 shows beam twiss parameter α of the electron gun as a function of axial coordinate, according to one embodiment of the invention.
Figure 7:
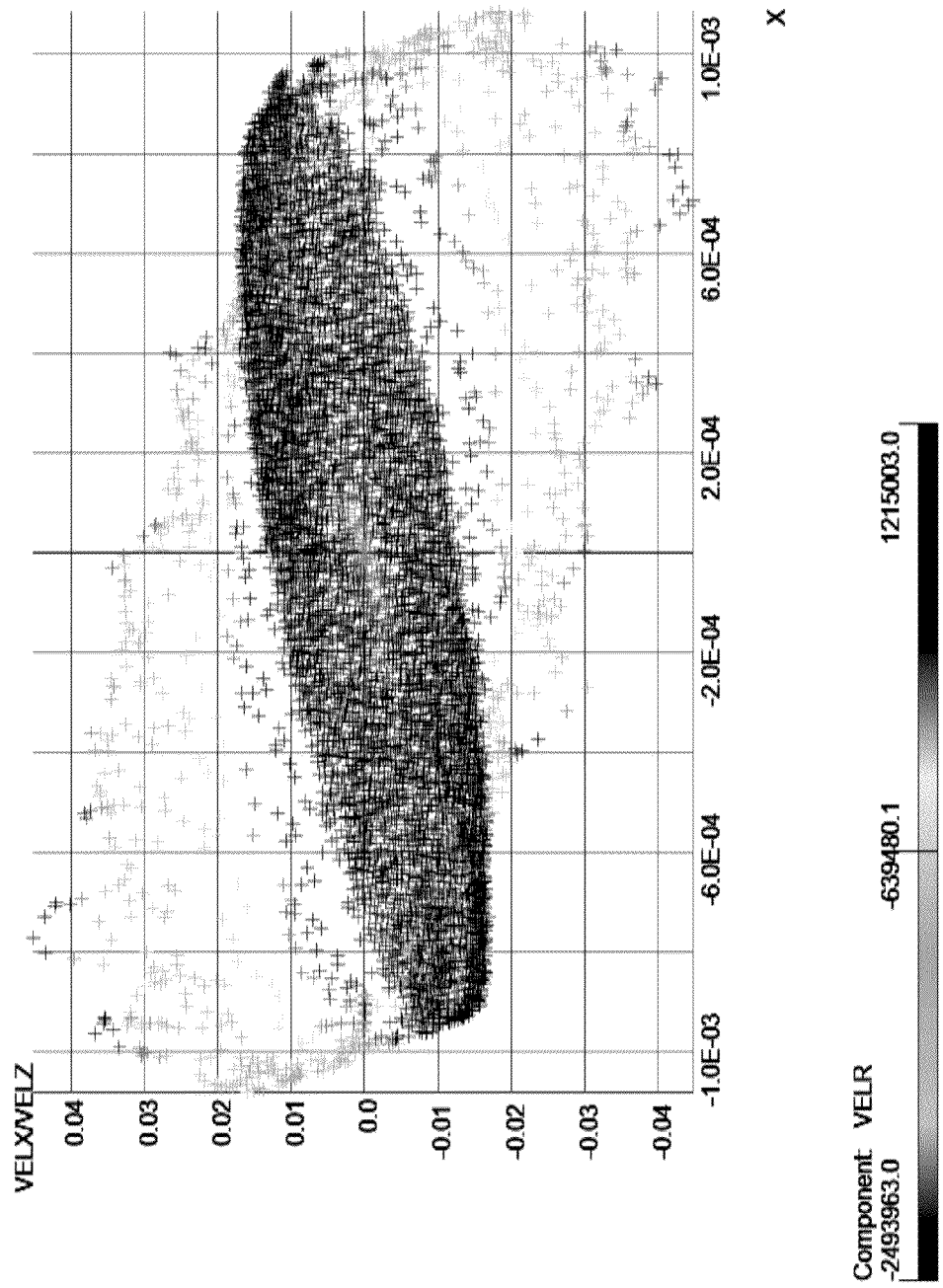
FIG. 7 shows a plot of transverse phase of the beam at the minimum rms emittance position, i.e 4.4 mm away from the cathode, according to one embodiment of the invention.
Figure 8:
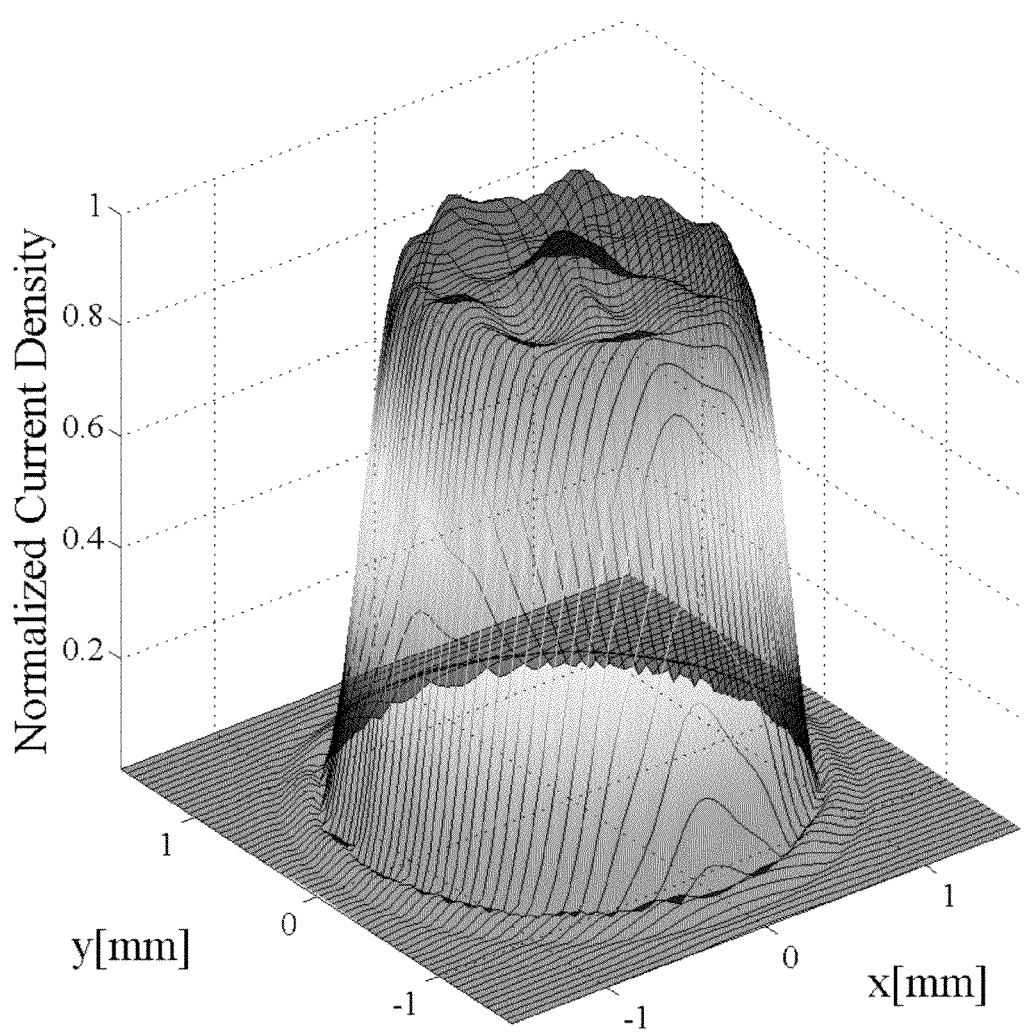
FIG. 8 shows a 3D plot of the electron beam profile at the point of minimum emittance, i.e. 4.4 mm away from the cathode, according to one embodiment of the invention.

The newly designed electron gun and its corresponding space charge solution are presented in FIG. 4. Here, the gun was positioned 1.3 m away from the mrT isocenter which correspond to a mean field strength of about B=0.18828 T. The transverse circular patch is positioned 4.4 mm away from the tip of the cathode and it indicates the optimum beam injection position in the accelerating waveguide. The electrons in the beam are experiencing a mean magnetic field strength B=0:18828 T. The magnetic beam confinement shown is a direct consequence of the Bush's theorem, which is valid only for axially symmetric configurations. The fact that the in-line MRI-linac configuration has axial symmetry is fundamental. This allows for an electron gun to function in external magnetic field without the need of decoupling the physics of the MRI scanner and the medical linac. The rms beam emittance $\epsilon_{rms}$ is an important figure of merit based on the effective volume occupied by the beam distribution in phase space. A small value of the rms emittance would correspond to close dynamic properties of the particles in the beam. A small value of the rms emittance is desired to increase the capture efficiency of the accelerating waveguide. The rms emittance can be defined based on phase space information as $$\epsilon_{x,rms} = \sqrt{\langle x^2 \rangle \langle x'^2 \rangle - \langle xx' \rangle^2}, \quad (1)$$

where $x'=dx/dz=dp_x/dp_z$ is the angle in the XZ-plane a particle makes with the beam axis of symmetry, i.e. Z-axis, in the paraxial approximation. The rms beam emmittance dependence on the axial coordinate is presented in FIG. 5. There are several minima in FIG. 5 but only the third minimum from the right can be used because at that position the particles in the beam are no longer accelerating. In FIG. 5 the cathode tip is positioned at 15 mm and the third minimum is 10:2 mm away from the tip. This is where the first cavity of the accelerating waveguide starts and the drift tube of the anode ends. Another important parameter that describes the degree of convergence of the beam is the Courant-Snyder a parameter, and it can be computed as $$\alpha_x = -\frac{\langle xx' \rangle}{\epsilon_{x,rms}}. \quad (2)$$

α is positive for convergent flow, zero when there is no radial motion, and negative for divergent flow. The α parameter dependence on the axial coordinate is presented in FIG. 6. The α parameter vanishes when the emittance reaches its minimum at 10:2 mm away from tip. Also, at that position the beam undergoes a transition from a diverging beam towards a converging beam, which makes this position even more desired as the end of the electron gun. The transverse X phase space is shown in FIG. 7. The particle dynamics is complicated by the existence of the external field and because of this the flow is not laminar. A laminar flow with a vanishing a parameter, i.e. no particle radial motion, would correspond to a horizontal line. The beam cross section is presented in FIG. 8. The conical shape of the cathode is essential in generating a plain beam. Any other cathode shape would generate a hollow beam, i.e. the beam cross section has a circular region inside with no particles.

Figure 9:
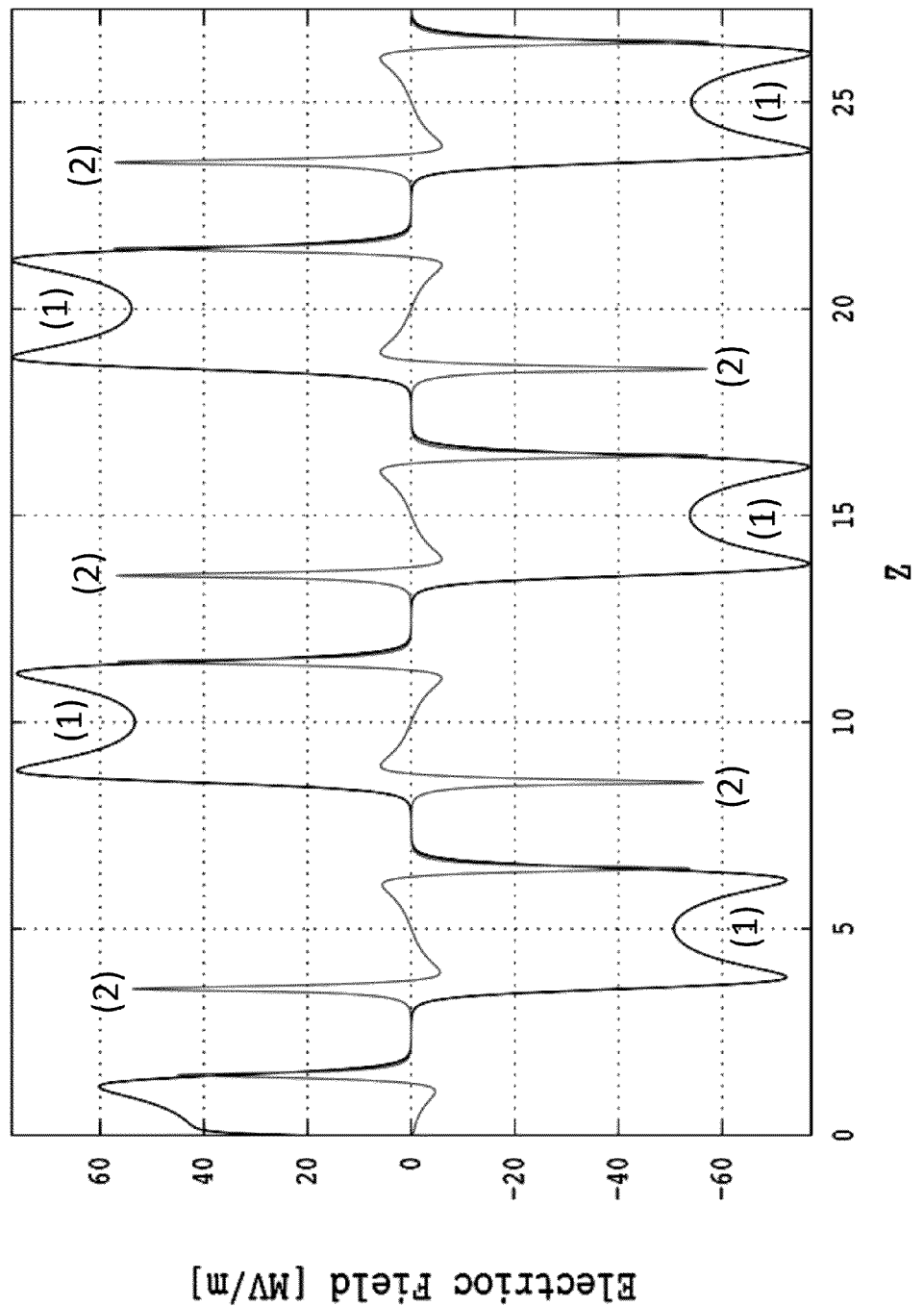
FIG. 9 shows a plot of the RF electric field along the accelerating waveguide at a phase value $\phi=45°$, according to one embodiment of the invention.

The accelerating RF electric field components are shown in FIG. 9 at a phase value φ=45°.

In this example, a robust method of image guidance for an in-line MRI-linac configuration was shown. A specially designed electron gun was simulated in the fringe field of an open bore split MRI magnet for local quasi-axial symmetric configurations. The beam characteristics proved to be suitable for injection into a medical linac. The linac model was also simulated under the same conditions as the electron gun. The simulations outcome shows there is no need for magnetic shielding as long as local quasi-axial symmetry is maintained. These findings allow for linac displacement from the axis of symmetry of the magnet to off axis positions with the linac aligned with the field lines such that the radiation beam is following the moving tumor.

FIG. 9 shows a plot of the RF electric field along the accelerating waveguide at a phase value φ=45°. The axial component (1) is plotted along the axis of symmetry. The radial component (2) is plotted along a line parallel to the axis of symmetry at a distance equal to the radius of the drift tubes in the linac.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example the MRI magnet can be actively and/or passively shielded and it can be used in an RLA configuration provided its fringe field satisfies the quasi-homogeneity condition, i.e. fringe field lines curvature is much bigger than the linac length. Under the same quasi-homogeneity condition a longer linac can be used for the purpose of increasing the energy of the delivered X-ray beam.

All such variations are considered to be within the scope and spirit of the present invention as defined by the following claims and their legal equivalents.

What is claimed:
1. An MRI-linac apparatus, comprising:
 a. an MRI scanner, wherein the MRI scanner comprises an open bore MRI magnet that is capable of generating a magnetic field having a fringe field, wherein said open bore MRI magnet comprises a doughnut-shape magnet, wherein said doughnut-shape comprises a center open bore that is symmetric to said doughnut-shape, wherein said center open bore comprises a cylindrical shape having a center axis, wherein said center axis of said center open bore is an axis of symmetry for said open bore MRI magnet; and
 b. a magnetically unshielded linac comprising an electron gun, wherein the electron gun is disposed to generate an electron beam in the presence of the fringe field, wherein the magnetically unshielded linac is displaced away from said axis of symmetry of said open bore MRI magnet, wherein the displaced magnetically unshielded linac is disposed to output a treatment beam that is displaced from an isocenter of said MRI-linac apparatus.

* * * * *